United States Patent [19]

Sharp et al.

[11] Patent Number: 4,814,155

[45] Date of Patent: Mar. 21, 1989

[54] METHOD OF SELECTIVE REDUCTION OF POLYHALOSILANES WITH ALKYLTIN HYDRIDES

[75] Inventors: Kenneth G. Sharp, Midland; John J. D'Errico, Fenton, both of Mich.

[73] Assignee: Dow Corning Corporation, Midland, Mich.

[21] Appl. No.: 78,444

[22] Filed: Jul. 27, 1987

[51] Int. Cl.$^4$ .................... C01B 33/08; C01B 33/04
[52] U.S. Cl. .................... 423/342; 423/347; 556/474
[58] Field of Search ................. 556/474; 423/342, 347

[56] References Cited

U.S. PATENT DOCUMENTS 3,043,857 7/1962 Jenkner ........................ 556/474 X
3,378,344 4/1968 Horn et al. .................... 556/474 X

OTHER PUBLICATIONS

"Chemical Abstracts", 97, 14119K, 1982.
"Chemical Abstracts", 101, 130803d, 1984.
"Chemical Abstracts", 11th Collective Index, Formula Index, p. 177F.

Primary Examiner—Paul F. Shaver
Attorney, Agent, or Firm—James E. Bittell

[57] ABSTRACT

The invention relates to the selective and stepwise reduction of polyhalosilanes by reacting at room temperature or below with alkyltin hydrides without the use of free radical intermediates. Alkyltin hydrides selectively and stepwise reduce the Si—Br, Si—Cl, or Si—I bonds while leaving intact any Si—F bonds. When two or more different halogens are present on the polyhalosilane, the halogen with the highest atomic weight is preferentially reduced.

25 Claims, No Drawings

METHOD OF SELECTIVE REDUCTION OF POLYHALOSILANES WITH ALKYLTIN HYDRIDES

STATEMENT OF GOVERNMENT RIGHTS

The U.S. Government has rights in this invention pursuant to Subcontract ZL-5-04074-6 under Prime Contract No. DE-AC02-83CH10093 awarded by the U.S. Department of Energy.

BACKGROUND OF THE INVENTION

The present invention relates to the discovery that alkyltin hydrides display selectivity with respect to both (a) the preferential reduction, under mild conditions, of one halogen to the exclusion of another halogen in a mixed halosilane and to (b), the stepwise reduction of halosilanes.

Substitution of hydrogen for chlorine in polychlorosilanes such as $(CH_3)SiCl_3$ is known and can be effected via reaction with trialkylsilanes in the presence of catalytic quantities of aluminum chloride. However, this catalyst is notoriously effective in promoting skeletal rearrangements (i.e., redistributions involving Si-C and/or Si-Si bonds).

Organotin hydrides have long been known as effective reducing agents in organic chemistry and their reactivity patterns have been well documented. Perhaps the most common use of tin hydrides is in the reduction of organic halides.

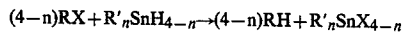

$$(4-n)RX + R'_nSnH_{4-n} \rightarrow (4-n)RH + R'_nSnX_{4-n}$$

The above reaction has a wide scope: R can be alkyl, aryl, acyl, propargyl, etc. The reaction conditions will vary with the R group (eg., aryl halides are more difficult to reduce than alkyl halides) and with the halide (for alkyl halides the order of reactivity is RI>RBr>RCl>>RF). These reactions proceed through free radical mechanisms and require the addition of free radical initiators.

U.S. Pat. No. 4,617,357, issued Oct. 14, 1986 to Pallie et al., teaches the reduction of residual chlorine in glycidyl compounds with certain organo-tin hydrides without the glycidyl group thereby being attacked.

Aono et al., U.S. Pat. No. 4,639,361, issued Jan. 27, 1987, teaches a process of preparing disilane $Si_2H_6$ from the reduction of hexachlorodisilane $Si_2Cl_6$ with a mixture of LiH and $LiAlH_4$.

Hiiro et al., U.S. Pat. No. 4,115,426, issued Sept. 19, 1978, teaches a method of preparing dialkylchlorosilanes by the selective dechlorination reduction of a dialkyldichlorosilane. The reducing agents in the preparation are sodium borohydride and sodium hydride.

Grady, et al., J. Org. Chem., vol. 34, p. 2014-2016, 1969, teaches the use of organotin hydrides for the stepwise free radical reduction of organic halides, such as geminal polyhalides, and simple carbonyl compounds. Grady et al. does not teach the selective stepwise or other reduction of halosilanes, nor does it teach reduction methods in the absence of free radical mechanisms. Similarly, Wilt, et al., J. Am. Chem. Soc., vol. 105, p. 5665-5675, 1983, teaches the reduction of a silicon-containing organic halides by organotin hydrides, but is limited to the reduction of alpha-halosilanes, i.e., the halogen atom is bonded to a carbon atom adjacent to a silicon atom but is not bonded directly to a silicon atom.

Organotin hydrides typically react with organohalides and unsaturated bonds via a free radical mechanism. These reactions either require heating or initiation by a free radical source.

U.S. Pat. No. 3,439,008, issued Apr. 15, 1969 to Berger, teaches and claims a method of reacting an organostannane and a halogenated Group IVb elemental material selected from the group consisting of a halosilane, a halogermane, and a halosiloxane. However, Berger requires the presence of a Group III metal compound promoter and does not teach or claim the selective, stepwise reduction of halosilanes.

There exists a need for a preferential reduction of one halogen species to the exclusion of another in molecules such as $SiF_2Br_2$ and other halomonosilanes.

SUMMARY OF THE INVENTION

The present invention relates to the selective and stepwise reduction of polyhalosilanes by reacting at room temperature or below with alkyltin hydrides without the use of free radical intermediates. Alkyltin hydrides selectively and stepwise reduce the Si—Br, Si—Cl, or Si—I bonds while leaving intact any Si—F bonds. When two or more different halogens are present on the polyhalosilane, the halogen with the highest atomic weight is preferentially reduced.

DETAILED DESCRIPTION

The present invention relates to a method of selective reduction of at least one of the silicon-halogen bonds of a halosilane or a polyhalosilane to a silicon-hydrogen bond, said method comprising contacting a halosilane or a polyhalosilane with an alkyltin hydride of the formula $R_xSnH_{(4-x)}$, wherein x is 3, 2, or 1, and wherein R is an alkyl group containing 1 to 10 carbon atoms, or an aryl group of 6 to 10 carbon atoms, whereby at least one of the silicon-halogen bonds of the halosilane or polyhalosilane is reduced to a silicon-hydrogen bond, and wherein the silicon-fluorine bonds, if any, of the halosilane or polyhalosilane remain intact.

By "halosilane" in the present invention is meant dihalosilanes and polyhalosilanes of the formula $X_mSiH_nF_yR^1_z$, where m is 1, 2, 3, or 4; n is 0, 1, or 2; y is 0, 1, 2, or 3; z is 0, 1, or 2; n+y+z is less than or equal to 3; m+n+y+z is equal to 4; X is independently selected from the group consisting of Cl, Br, or I; and $R^1$ is an alkyl group having one to twenty carbon atoms. By "polyhalosilane" in the present invention is meant halosilanes as defined above wherein m+y is equal to two, three or four. To be included in the group "polyhalosilane" are the halosilanes, as defined above, in which two or more halogens are independently selected from the group consisting of fluorine, chlorine, bromine, and iodine. By "stepwise reduction" in the present invention is meant the essentially complete conversion of, for example, $X^1_aSiX^2_b$ into $X^1_{(a-1)}SiHX^2_b$, where $X^1$ has a higher atomic weight than does $X^2$.

The organotin hydrides used in the method of the present invention were allowed to react with a variety of halosilanes, including fluorohalo monosilanes. The fluorohalo monosilanes can be obtained, for example, from the redistribution reaction shown below

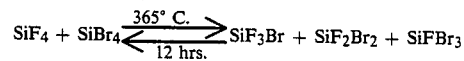

$$SiF_4 + SiBr_4 \xrightleftharpoons[\text{12 hrs.}]{365° C.} SiF_3Br + SiF_2Br_2 + SiFBr_3$$

Organotin hydrides were allowed to react with SiF$_3$Br in the gas phase to produce a group of reduction products:

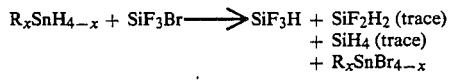
$$R_xSnH_{4-x} + SiF_3Br \longrightarrow SiF_3H + SiF_2H_2 \text{ (trace)}$$
$$+ SiH_4 \text{ (trace)}$$
$$+ R_xSnBr_{4-x}$$

where x=2, R=CH$_3$, and where x=3, R=CH$_3$ or CH$_3$CH$_2$.

According to the present invention, alkyltin hydrides selectively reduce the Si—Br bond of SiF$_3$Br to form SiF$_3$H together with traces of SiF$_2$H$_2$ and SiH$_4$ detected only at very low levels. When an excess of the tin hydride is added to the reaction mixture, there is no further reduction of the SiF$_3$H observed after several hours. The same results were observed regardless of the tin hydride employed. However, a comparable reduction with Vitride (NaAlH$_2$(OCH$_2$CH$_2$OCH$_3$)$_2$) as the reducing agent resulted in both the Si—Br and Si—F bonds being reduced, producing SiH$_4$ in >90% yield. This illustrates the selectivity and mildness of the alkyltin hydride reductions of the present invention.

Tin hydrides were allowed to react with SiF$_2$Br$_2$ using a 2:1 molar ratio of Si—Br to Sn—H. There was very little SiF$_2$H$_2$ observed in the reaction mixture. The major product was the stepwise reduction product SiF$_2$HBr. This was characterized by the infrared (Si—H stretch at 2283 cm$^{-1}$) $^1$H and $^{19}$F nmr spectroscopy. Addition of a second equivalent of tin hydride resulted in the disappearance of the band at 2283 cm$^{-1}$ of the infrared spectrum due to SiF$_2$HBr and the appearance of bands at 2251 cm$^{-1}$ for SiF$_2$H$_2$. (See Example 2.) To the best knowledge of the inventors, this represents the first time that SiF$_2$HBr has been synthesized.

According to the present invention, (CH$_3$)$_3$SnH was allowed to react with SiCl$_4$ whereby the predominant reduction product was HSiCl$_3$.

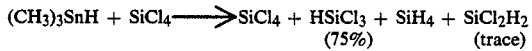
$$(CH_3)_3SnH + SiCl_4 \longrightarrow SiCl_4 + HSiCl_3 + SiH_4 + SiCl_2H_2$$
$$(75\%) \quad \text{(trace)}$$

(CH$_3$)$_3$SnH was then allowed to react with HSiCl$_3$ to produce H$_2$SiCl$_2$ (75% yield) and SiH$_4$ (25%). Some of the HSiCl$_3$ did not react; what did react went 75% to H$_2$SiCl$_2$. This indicates the stepwise reductive properties of the organotin hydrides as compared to conventional reducing agents such as LiAlH$_4$, where reaction of either SiCl$_4$ or HSiCl$_3$ with LiAlH$_4$ would proceed to SiH$_4$.

The methods of the present invention can reduce in a stepwise manner silicon- and halogen-containing materials which contain two or more halogens independently selected from the group consisting of chlorine, bromine, and iodine. Fluorine may also be present but is not reduced. The halogen with the highest atomic weight is preferentially reduced by the methods of the present invention.

The methods of the present invention could be conducted by those skilled in the art under static or dynamic conditions, at elevated or cooled reaction temperatures, using reactants in the liquid (i.e., condensed) phase or gas phase.

The methods of the present invention are useful in preparing partially reduced halosilanes which possess utility in a wide variety of applications, such as forming crystalline silicon and in RSiCl$_3$ reactions. SiF$_2$HBr is produced for the first time by the method of the present invention. The materials produced by the method of the present invention are useful as precursors for the chemical vapor deposition (CVD) and plasma enhanced CVD of various halosilane compounds in the generation of amorphous silicon semiconducting films, and films for the protection of surfaces. The materials are also useful as precursors for disilane formation by Wurtz coupling reaction of a fluorobromosilane, for example, or as precursors in the photolysis of a fluorohydridosilane. The materials produced by the method of the present invention are also useful as precursors for the hydrosilylation reaction with an unsaturated hydrocarbon.

EXAMPLES

The following examples were performed on a high vacuum line at room temperature. Each reactant was allowed to expand into a constant volume to a specific pressure, typically 10–20 torr. The progress of the reactions was monitored by the appearance of bands in the Si—H stretching region of the infrared spectrum (2400–2000 cm$^{-1}$), as well as by the disappearance of the Sn—H stretches (1900–1750 cm$^{-1}$). Both of these regions are free of interferences such as combination and overtone bands. The frequencies cited refer to the SiH stretch. The predominant Sn by-products of these reactions were shown to be R$_x$SnBr$_{(4-x)}$ and R$_x$SnCl$_{(4-x)}$ by their $^1$H nmr and IR spectra.

1. Reduction of SiF$_3$Br to SiF$_3$H with (CH$_3$)$_3$SnH, (CH$_3$CH$_2$)$_3$SnH or (CH$_3$)$_2$SnH$_2$.

One equivalent of (CH$_3$)$_3$SnH was allowed to react with SiF$_3$Br at room temperature for approximately 7 hours in a sealed flask attached to a high vacuum line. The reaction mixture was analyzed by Fourier transform spectroscopy. The predominant Si-containing product (>90% yield) was SiF$_3$H (2315 cm$^{-1}$) together with traces of SiF$_2$H$_2$ (2251 cm$^{-1}$) and SiH$_4$ (2186 cm$^{-1}$). The addition of excess (CH$_3$)$_3$SnH did not result in the further reduction of SiF$_3$H. The reduction of SiF$_3$Br was repeated using (CH$_3$CH$_2$)$_3$SnH or (CH$_3$)$_2$SnH$_2$ and the same results were obtained.

2. Reduction of SiF$_2$Br$_2$ to SiF$_2$HBr with (CH$_3$)$_3$SnH, (CH$_3$CH$_2$)$_3$SnH, or (CH$_3$)$_2$SnH$_2$. Synthesis of SiF$_2$HBr.

One equivalent of (CH$_3$)$_3$SnH was allowed to react with SiF$_2$Br$_2$ in a 1:1, Sn—H:SiF$_2$Br$_2$ molar ratio at room temperature for approximately 12 hours in a sealed flask attached to a high vacuum line. The reaction mixture was then passed through a trap cooled to −131 degrees Centigrade into a trap cooled to −196 degrees Centigrade. The material trapped at −196 degrees Centigrade was analyzed by infrared, $^1$H, and $^{19}$F nmr spectroscopies. The major component (>90% yield) exhibited the following spectral data: IR (cm$^{-1}$) 2283 (m), 979 (s), 969 (s), 888 (vs), 832 (s), 826 (s), 469 (m). $^1$H nmr (200 MHz, D$_8$-toluene): triplet centered at 4.99 ppm, J$_{H-F}$=80.5 Hz, J$_{F-29Si}$=378.8 Hz. $^{19}$F nmr (188 MHz, D$_8$-toluene): doublet centered at 81.7 ppm (upfield from external CFCl$_3$), J$_{F-H}$=80.4 Hz, J$_{F-29Si}$=320.0 Hz. These data indicate the structural formula is SiF$_2$HBr. There were also peaks in the IR and nmr spectra of SiF$_2$HBr due to small amounts of SiF$_3$H probably formed from the reduction of small amounts of SiF$_3$Br present as an impurity in the starting material.

Addition of a second equivalent of (CH$_3$)$_3$SnH resulted in the disappearance of the SiF$_2$HBr (2283 cm$^{-1}$)

and the formation of SiF$_2$H$_2$ (2251 cm$^{-1}$). There was no further reduction of SiF$_2$H$_2$ upon addition of excess organotin hydride.

The above example was repeated with (CH$_3$CH$_2$)$_3$SnH and (CH$_3$)$_2$SnH$_2$, separately, and the results obtained were the same as those described above for the reduction with (CH$_3$)$_3$SnH.

3. Reduction of SiFBr$_3$ with (CH$_3$)$_3$SnH, (CH$_3$CH$_2$)$_3$SnH, or (CH$_3$)$_2$SnH$_2$.

Using the procedure of Example 2, three equivalents of (CH$_3$)$_3$SnH were allowed to react with one equivalent of SiFBr$_3$ at room temperature. After 30 minutes, an infrared spectrum indicated the presence of SiH$_4$ (2186 cm$^{-1}$), SiF$_2$H$_2$ (2251 cm$^{-1}$), and a small amount of SiF$_3$H (2315 cm$^{-1}$). There was no SiFH$_3$ observed in the reaction mixture. The SiH$_4$ is present due to the high propensity of SiFH$_3$ to redistribute F and H to produce SiH$_4$ and SiF$_2$H$_2$. In a similar manner, the SiF$_3$H is believed to be from SiF$_2$H$_2$/SiFH$_3$ redistribution.

Three equivalents of (CH$_3$)$_3$SnH and one equivalent of SiFBr$_3$ were condensed into a trap held at −196 degrees Centigrade. A −78 degrees Centigrade bath was then placed around the trap and an infrared spectrum of the reaction mixture was obtained after 90 minutes. The spectrum contained bands due to SiFH$_3$ (2206, 2196, 991, 873, 729 cm$^{-1}$).

4. Reduction of SiCl$_4$ with Organotin Hydrides.

Equimolar quantities of SiCl$_4$ and (CH$_3$)$_3$SnH were allowed to react in a sealed container at room temperature. After 40 minutes, an infrared spectrum was obtained which indicated that no reaction had occurred. An infrared spectrum obtained after 2.5 hours indicated the presence of a major product, SiCl$_3$H, (2260 cm$^{-1}$) together with substantially lesser amounts of SiCl$_2$H$_2$ (2236 cm$^{-1}$) and SiH$_4$ (2186 cm$^{-1}$). The reaction was allowed to proceed for 36 hours, at which point the (CH$_3$)$_3$SnH had completely reacted. The Si-containing products included unreacted SiCl$_4$, SiCl$_3$H (70-75% of the reduced species), and small amounts of SiCl$_2$H$_2$ and SiH$_4$.

Repeating the reduction with (CH$_3$CH$_2$)$_3$SnH and (CH$_3$)$_2$SnH$_2$, separately, replacing the (CH$_3$)$_3$SnH did not change the results.

5. Reduction of SiCl$_3$H with Organotin Hydrides. (condensed phase)

Equimolar quantities of SiCl$_3$H and (CH$_3$)$_3$SnH were allowed to react at room temperature. Approximately 12 hours were required for the Sn—H material to be consumed, at which point unreacted SiCl$_3$H (2260 cm$^{-1}$) was still present in the mixture. The major products of the reaction were SiCl$_2$H$_2$ (43% total yield, representing 70-75% of the reduced species) (2236 cm$^{-1}$) and SiH$_4$ (18% of total yield, 25% of the reduced species) (2186 cm$^{-1}$). There was approximately 38% unreacted SiCl$_3$H in the product mixture. There was no evidence of SiClH$_3$ (2212 cm$^{-1}$) in the mixture. The same results were obtained regardless of the organotin hydride employed.

6. Reduction of (CH$_3$)SiCl$_3$ with Organotin Hydrides.

Equimolar quantities of (CH$_3$)SiCl$_3$ and (CH$_3$)$_3$SnH were allowed to react to room temperature over night. An infrared spectrum of the mixture indicated that most of the starting materials remained unreacted, with only a trace of (CH$_3$)SiCl$_2$H (2218 cm$^{-1}$) being formed. The amount of (CH$_3$)SiCl$_2$H did not increase significantly, even after warming the mixture to 60–65 degrees Centigrade for 12 hours. There was also no further reduction of the (CH$_3$)SiCl$_2$H. The same results were obtained regardless of the organotin hydride employed.

7. Reactions of (CH$_3$)$_2$GeH$_2$ with SiCl$_3$H or SiFBr$_3$.

Equimolar amounts of (CH$_3$)$_2$GeH$_2$ and SiCl$_3$H (or SiFBr$_3$) were allowed to react together in the gas phase at room temperature. In each case, no reaction was observed (IR spectroscopy) after 12 hours.

8. Reactions of (CH$_3$)$_3$SiH with SiF$_2$Br$_2$ or SiF$_3$Br.

Equimolar amounts of (CH$_3$)$_3$SiH and SiF$_2$Br$_2$ (or SiF$_3$Br) were allowed to react at room temperature for 12 hours. In each case, no reaction was observed (IR spectroscopy) after 12 hours.

9. Reaction of (CH$_3$)$_3$SnH with SiF$_3$Cl.

Equimolar quantities of SiF$_3$Cl and (CH$_3$)$_3$SnH were condensed together and allowed to react for 60 hours at room temperature. The only product observed from this reaction was SiF$_3$H. There was no further reaction observed upon the addition of excess (CH$_3$)$_3$SnH.

10. Reaction of (CH$_3$)$_3$SnH with SiBr$_4$. (Condensed phase)

Equimolar quantities of SiBr$_4$ and (CH$_3$)$_3$SnH were condensed together and allowed to react for 1 hour at room temperature. An infrared spectrum of the reaction mixture indicated that all of the (CH$_3$)$_3$SnH had been consumed. Aside from some unreacted SiBr$_4$, the products of the reaction consisted of SiH$_4$ and SiBr$_3$H (ca. 60:40 molar ratio). There was no evidence of SiBr$_2$H$_2$ in the infrared spectrum of the mixture.

11. Reaction of (CH$_3$)$_3$SnH with SiBr$_4$. (gas phase)

Equimolar quantities of SiBr$_4$ and (CH$_3$)$_3$SnH were allowed to react for 12 hours at room temperature in the gas phase. An infrared spectrum of the reaction mixture indicated that the only reduced species present was SiBr$_3$H; there was no evidence of SiBr$_2$H$_2$ or SiH$_4$.

12. Reaction of (CH$_3$)$_3$SnH with SiBr$_4$. (gas phase)(2 equiv.)

The procedure in Example 11 was repeated and the resulting SiBr$_3$H was allowed to react with a second equivalent of (CH$_3$)$_3$SnH. After 12 hours at room temperature, an infrared spectrum of the reaction mixture indicated the presence of unreacted SiBr$_3$H, SiH$_4$, and a trace of SiBr$_2$H$_2$.

13. Reaction of (CH$_3$)$_3$SnH with SiBrCl$_3$.

Equimolar quantities of (CH$_3$)$_3$SnH and SiBrCl$_3$ were condensed together in a vacuum line trap and allowed to warm to room temperature. An infrared spectrum of the reaction mixture was obtained after three hours at room temperature. The only Si—H containing products were SiCl$_3$H and SiH$_4$ (due to redistribution) (ca: 4:1 molar ratio). There was also some SiCl$_4$ observed in the reaction mixture. This reaction shows the preferential reduction of the halogen with the highest atomic weight before the reduction of any of the lower atomic weight halogen atoms.

That which is claimed is:

1. A method of reduction of at least one of the silicon-X bonds of a halosilane to a silicon-hydrogen bond, wherein the halosilane is of the formula X$_m$SiH$_n$F$_y$R$^1_z$, where m is 1, 2, 3, or 4; n is 0, 1, or 2; y is 0, 1, 2, or 3; z is 0, 1, or 2; n+y+z is less than or equal to 3; m+n+y+z is equal to 4; X is independently selected from the group consisting of Cl, Br, or I; and R$^1$ is an alkyl group having one to twenty carbon atoms, said method consisting essentially of contacting the halosilane with an alkyltin hydride of the formula R$^2_x$SnH$_{(4-x)}$, wherein x is 3, 2, or 1, and wherein R$^2$ is an alkyl group containing 1 to 10 carbon atoms, or an aryl group of 6 to 10 carbon atoms, whereby at least one of the silicon-X bonds of the halosilane is reduced to a silicon-hydrogen bond.

2. A method of reduction of a silicon-halogen bond of a polyhalosilane to a silicon-hydrogen bond wherein the halogens of the polyhalosilane are independently selected from the group consisting of fluorine, chlorine, bromine, and iodine, and wherein when there are 2 or more different halogens present, the halogen with the highest atomic weight is preferentially reduced, said method consisting essentially of contacting said polyhalosilane with an alkyltin hydride of the formula $R^3{}_x SnH_{(4-x)}$, wherein x is 3, 2, or 1, and wherein $R^3$ is an alkyl group containing 1 to 10 carbon atoms, or an aryl group of 6 to 10 carbon atoms.

3. A method as claimed in claim 1, wherein the reduction of the silicon-X bond to a silicon-hydrogen bond is selective, wherein when m is not 4, and wherein when X is bromine and y is not zero, the silicon-fluorine bond of the halosilane remains intact.

4. A method as claimed in claim 1, wherein the reduction of the silicon-X bond to a silicon-hydrogen bond is selective, wherein when m is not 4, and wherein when X is iodine and y is not zero, the silicon-fluorine bond of the halosilane remains intact.

5. A method as claimed in claim 1, wherein the reduction of the silicon-X bond to a silicon-hydrogen bond is selective, wherein when m is not 4, and wherein when X is chlorine and y is not zero, the silicon-fluorine bond of the halosilane remains intact.

6. A method as claimed in claim 1, wherein the reduction of the silicon-X bond to a silicon-hydrogen bond is selective, wherein when m is 2, 3, or 4, and wherein when one of the X moieties is bromine and another is chlorine, the silicon-bromine bond of the halosilane is reduced and the silicon-chlorine bond and the silicon-fluorine bond, if any, of the halosilane remain intact.

7. A method as claimed in claim 1, wherein the reduction of the silicon-X bond to a silicon-hydrogen bond is selective, wherein when m is 2, 3, or 4, and wherein when one of the X moieties is bromine and another is iodine, the silicon-iodine bond of the halosilane is reduced and the silicon-bromine bond and the silicon-fluorine bond and silicon-chlorine bond, if any, of the halosilane remain intact.

8. A method as claimed in claim 1, wherein the reduction of the silicon-X bond to a silicon-hydrogen bond is selective, wherein when m is 2, 3, or 4, and wherein when one of the X moieties is chlorine and another is iodine, the silicon-iodine bond of the halosilane is reduced and the silicon-chlorine bond and the silicon-fluorine bond, if any, of the halosilane remain intact.

9. A method as claimed in claim 1, wherein the reduction of the silicon-X bond to a silicon-hydrogen bond is selective, wherein when m is 1, 2, or 3, and wherein when y is 1, 2, or 3 and X is chlorine, a silicon-chlorine bond of the halosilane is reduced and the silicon-fluorine bond or bonds of the halosilane remain intact.

10. A method as claimed in claim 1 wherein the alkyltin hydride is $(CH_3)_3SnH$.

11. A method as claimed in claim 1 wherein the alkyltin hydride is $(CH_3CH_2)_3SnH$.

12. A method as claimed in claim 1 wherein the alkyltin hydride is $(CH_3)_2SnH_2$.

13. A method as claimed in claim 1 wherein silicon tetrachloride is reduced to trichlorosilane.

14. A method as claimed in claim 1 wherein trichlorosilane is reduced to dichlorosilane.

15. A method as claimed in claim 1 wherein methyltrichlorosilane is reduced to methyldichlorosilane.

16. A method as claimed in claim 2 wherein the polyhalosilane contains two or more different halogens independently selected from the group consisting of fluorine, chlorine, bromine, and iodine.

17. A method as claimed in claim 1 wherein the halosilane is $SiF_2Br_2$.

18. A method as claimed in claim 1 wherein the halosilane is $SiFBr_3$.

19. A method as claimed in claim 1 wherein the reduction is conducted under static conditions.

20. A method as claimed in claim 1 wherein the reduction is conducted under dynamic conditions.

21. A method as claimed in claim 1 wherein the reduction is conducted at elevated temperatures.

22. A method as claimed in claim 1 wherein the reduction is conducted at below room temperature.

23. A method as claimed in claim 1 wherein the reduction is conducted in the liquid phase.

24. A method as claimed in claim 1 wherein the reduction is conducted in the gas phase.

25. A method as claimed in claim 1 wherein $SiF_3Br$ is reduced to $SiF_3H$.

* * * * *